United States Patent
Buraczenski et al.

(10) Patent No.: US 12,011,529 B2
(45) Date of Patent: *Jun. 18, 2024

(54) NON-TOUCH COMMUNICATION WITH A DIALYSIS MACHINE USING A CONNECTED HEALTH SYSTEM

(71) Applicant: Fresenius Medical Care Holdings, Inc., Waltham, MA (US)

(72) Inventors: Matthew Buraczenski, Holden, MA (US); Harvey Cohen, Newton, MA (US); Kulwinder S. Plahey, Martinez, CA (US); John A. Biewer, Waltham, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/949,750

(22) Filed: Sep. 21, 2022

(65) Prior Publication Data
US 2023/0019082 A1 Jan. 19, 2023

Related U.S. Application Data

(63) Continuation of application No. 15/862,765, filed on Jan. 5, 2018, now Pat. No. 11,491,270.

(51) Int. Cl.
*A61M 1/28* (2006.01)
*A61M 1/14* (2006.01)
(Continued)

(52) U.S. Cl.
CPC .............. *A61M 1/28* (2013.01); *A61M 1/152* (2022.05); *A61M 1/159* (2022.05); *G06F 3/167* (2013.01);
(Continued)

(58) Field of Classification Search
CPC . A61M 1/28; G06F 3/167; H04B 1/40; G16H 40/67
(Continued)

(56) References Cited

U.S. PATENT DOCUMENTS 7,981,281 B2   7/2011   Yu et al.
8,529,496 B2   9/2013   Britton et al.
(Continued)

FOREIGN PATENT DOCUMENTS

DE   102017201451 A1 *   8/2018   ......... A61B 17/3403
DE   102017201452          8/2018
(Continued)

OTHER PUBLICATIONS

De Lissovoy, Gregory V.; The Diffusion of New Medical Technology in the Presence of Health Insurance: The Cases of Renal Dialysis and Home; The University of North Carolina at Chapel Hill. ProQuest Dissertations Publishing, 1987. 8722284. (Year: 1987).*

(Continued)

*Primary Examiner* — Hiep V Nguyen
(74) *Attorney, Agent, or Firm* — Fish & Richardson P.C.

(57) ABSTRACT

A dialysis system includes include a home dialysis machine and a home gateway device in communication with a cloud-based application via a connected health system. The gateway device has voice recognition capabilities. A user can provide spoken information to the gateway device, and the gateway device can cause one or more actions to be performed. The gateway device may cause a dialysis function to be performed by the dialysis machine, or data to be input into the dialysis machine. The gateway device can also communicate with one or more other systems (e.g., remote systems) via the cloud-based application. In some examples, the cloud-based application can communicate with an order (Continued)

management system to allow the user to order medical supplies (e.g., for use with the dialysis machine) via the gateway device. The gateway device can provide two-way conversational capability (e.g., back and forth communication) between the user and the gateway device.

20 Claims, 6 Drawing Sheets

(51) Int. Cl.
| | |
|---|---|
| G06F 3/16 | (2006.01) |
| G10L 15/22 | (2006.01) |
| G16H 20/40 | (2018.01) |
| G16H 40/20 | (2018.01) |
| G16H 40/63 | (2018.01) |
| G16H 40/67 | (2018.01) |
| H04B 1/40 | (2015.01) |

(52) U.S. Cl.
CPC ............ *G16H 20/40* (2018.01); *G16H 40/20* (2018.01); *G16H 40/63* (2018.01); *G16H 40/67* (2018.01); *A61M 2205/50* (2013.01); *G10L 15/22* (2013.01); *H04B 1/40* (2013.01)

(58) Field of Classification Search
USPC .......................................................... 705/2
See application file for complete search history.

(56) References Cited

U.S. PATENT DOCUMENTS

| | | | |
|---|---|---|---|
| 8,698,741 | B1 | 4/2014 | Wang et al. |
| 9,050,411 | B2 | 6/2015 | Kelly et al. |
| 9,178,891 | B2 | 11/2015 | Wang et al. |
| 9,251,310 | B2 | 2/2016 | McNally et al. |
| 9,514,283 | B2 | 12/2016 | Childers et al. |
| 9,582,645 | B2 | 2/2017 | Yu et al. |
| 9,839,735 | B2 | 3/2017 | Tanebaum et al. |
| 9,675,745 | B2 | 6/2017 | Kelly et al. |
| 9,690,905 | B2 | 6/2017 | Yu et al. |
| 9,697,334 | B2 | 7/2017 | Yu et al. |
| 9,800,663 | B2 | 10/2017 | Arrizza |
| 9,940,603 | B1 | 4/2018 | Caven et al. |
| 9,861,733 | B2 | 6/2018 | Burbank et al. |
| 2007/0100660 | A1 | 5/2007 | Carosso et al. |
| 2009/0204513 | A1* | 8/2009 | Tirinato ............. G06Q 30/0639 705/28 |
| 2010/0042439 | A1 | 2/2010 | Martinez et al. |
| 2010/0138534 | A1 | 6/2010 | Mutnuru et al. |
| 2013/0131574 | A1 | 5/2013 | Cosentino et al. |
| 2013/0144757 | A1 | 6/2013 | Bauer et al. |
| 2013/0172806 | A1 | 7/2013 | Griessmann et al. |
| 2013/0297330 | A1 | 11/2013 | Kamen et al. |
| 2013/0310726 | A1* | 11/2013 | Miller .................. A61M 1/288 717/173 |
| 2015/0370973 | A1 | 12/2015 | Jones |
| 2016/0206800 | A1 | 6/2016 | Tanenbaum et al. |
| 2016/0261974 | A1 | 9/2016 | Arrizza |
| 2017/0065757 | A1 | 3/2017 | Tanebaum et al. |
| 2017/0076069 | A1 | 3/2017 | Moissl et al. |
| 2017/0087290 | A1 | 3/2017 | Medina et al. |

FOREIGN PATENT DOCUMENTS

| | | | | |
|---|---|---|---|---|
| WO | WO-2016019345 A1 * | 2/2016 | ............ | G06F 19/00 |
| WO | WO-2016090315 A1 * | 6/2016 | ............ | A47B 81/00 |
| WO | WO 2018/138330 | 8/2018 | | |

OTHER PUBLICATIONS

Haack et al., "Security Analysis of the Amazon Echo," May 18, 2017, Retrieved from the Internet: URL <https://courses.csail.mit.edu/6.857/2017/project/8.pdf>, 14 pages.
International Preliminary Report on Patentability in Application No. PCT/US2018/067076, dated Jul. 7, 2020, 10 pages.
International Search Report and Written Opinion in Application No. PCT/US2018/067076, dated Apr. 2, 2019, 14 pages.
Pullen, "Amazon Echo Ultimate User's Guide Time," Feb. 18, 2016, Retrieved from the Internet: URL <http://time.com/4227833/amazon-echo-user-guide/>, 7 pages.
Wang, "Location, Location, Location? A Study of peritoneal dialysis services in the United States," The University of North Carolina at Chapel Hill, 2008, 191 pages.

\* cited by examiner

NON-TOUCH COMMUNICATION WITH A DIALYSIS MACHINE USING A CONNECTED HEALTH SYSTEM

CROSS-REFERENCE TO RELATED APPLICATIONS

This application is a continuation application of and claims the benefit of priority to U.S. application Ser. No. 15/862,765, filed on Jan. 5, 2018, the contents of which are hereby incorporated by reference.

TECHNICAL FIELD

This disclosure relates to non-touch communication with a dialysis machine.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Automated PD machines called PD cyclers are designed to control the entire PD process so that it can be performed at home usually overnight without clinical staff in attendance. This process is termed continuous cycler-assisted PD (CCPD). Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

Dialysis machines are typically equipped with interfaces for receiving inputs and providing information to users.

SUMMARY

In an aspect, a dialysis system includes a dialysis machine and a gateway device. The gateway device is configured to receive spoken input from a user. The gateway device includes a microphone configured to receive audio input, and a control unit. The control unit is configured to identify one or more spoken words based on the audio input received at the microphone, and cause the dialysis machine to perform an action based on the identified one or more spoken words.

Implementations can include one or more of the following features.

In some implementations, the dialysis machine and the gateway device are configured to communicate through a wireless connection.

In some implementations, the action includes setting or modifying one or more parameters on the dialysis machine.

In some implementations, the action includes entering patient information into the dialysis machine.

In some implementations, the patient information entered into the dialysis machine is presented by a display of the dialysis machine.

In some implementations, the microphone is configured to receive second audio input, and the control unit is configured to identify one or more spoken words based on the second audio input, update the entered patient information based on the identified one or more spoken words, and cause the updated entered patient information to be presented by the display.

In some implementations, the gateway device includes a speaker configured to output spoken words to the user.

In some implementations, the gateway device is configured to provide two-way conversational capability between the user and the gateway device.

In some implementations, the control unit is configured to cause the speaker to generate a spoken response to the user based on the identified one or more spoken works, identify one or more spoken words based on second audio input received at the microphone in response to the spoken response generated by the speaker, and cause the dialysis machine to perform a second action based on the identified one or more spoken words based on the second audio input.

In some implementations, the gateway device is configured to communicate with one or more remote systems through a cloud-based application.

In some implementations, the action is determined at least in part by the one or more remote systems.

In some implementations, the gateway device is configured to communicate with an order management system through the cloud-based application.

In some implementations, the order management system is configured to receive, from the gateway device, via the cloud-based application, a request to place an order for a medical item from the user, provide, to the gateway device, via the cloud-based application, information related to a prior order placed by the user for the medical item, and receive, from the gateway device, via the cloud-based application, confirmation to place the order. A speaker of the gateway device provides, to the user, spoken output about the information related to the prior order.

In some implementations, the order is placed upon the user providing a passcode to the gateway device.

In some implementations, the request to place the order and the confirmation to place the order is provided by the user through spoken words.

In some implementations, the order management system is configured to determine an estimated inventory of a medical item at the location of the dialysis machine, compare the estimated inventory of the medical item to an actual inventory of the medical item at the location of the dialysis machine, and recommend an order for the medical item to be placed based on a current or anticipated shortage of the item.

In some implementations, the current or anticipated shortage of the item is determined by a rules based engine based on one or more of a rate of consumption of the item, a shipping time of the item, a frequency of use of the item, or an availability of the item.

In some implementations, the rules based engine is located at the gateway device or the order management system.

In some implementations, a speaker of the gateway device provides, to the user, spoken output about the recommended order.

In some implementations, the order management system is configured to receive, from the gateway device, via the cloud-based application, confirmation to place the recommended order provided by the user through spoken words.

In some implementations, the recommend order is placed upon the user providing a passcode to the gateway device.

In another aspect, a method includes receiving, by a gateway device in communication with a dialysis machine, audio input from a user, identifying one or more spoken words based on the audio input, and causing the dialysis machine to perform an action based on the identified one or more spoken words.

In another aspect, one or more non-transitory computer-readable medium store instructions operable to cause a computing device to perform operations including receiving, by a computing device in communication with a dialysis machine, audio input from a user, identifying one or more spoken words based on the audio input, and causing the dialysis machine to perform an action based on the identified one or more spoken words.

Implementations can include one or more of the following advantages.

In some implementations, the systems and techniques described herein can promote cleanliness and sterilization in a dialysis environment. For example, a user who issues a voice-based input to the dialysis system does not need to make physical contact with the dialysis system to control it, thereby reducing the risk of spreading germs and eliminating the need for the user to wear gloves.

In some implementations, dialysis systems with voice recognition capability allow a user to more quickly provide instructions and/or other information to the dialysis system. Such data entry can be especially helpful in a home dialysis context, particularly for users who have difficulty seeing/reading a display of the dialysis system, users who have difficulty manually inputting data into a user interface (e.g., a touch screen display) of the dialysis system, users who are unprepared or unfit to manually input data (e.g., users who are disoriented due to being awoken in the middle of the night, unable to see due to dark lighting conditions or not having glasses available, etc.).

Other aspects, features, and advantages of the invention will be apparent from the description and drawings, and from the claims.

DESCRIPTION OF DRAWINGS

Like reference symbols in the various drawings indicate like elements.

DETAILED DESCRIPTION

A dialysis system can include a home dialysis machine and a home gateway device in communication with a cloud-based application via a connected health system. The gateway device can include a microphone and a control unit that provide voice recognition capabilities to the gateway device. For example, in some implementations, the gateway device is configured to identify commands, questions, and/or answers that are spoken by a user. The speech may cause the gateway device to perform one or more actions, including causing the dialysis machine to carry out a function (e.g., a dialysis function). Alternatively, the speech may cause the gateway device to communicate with one or more other systems (e.g., remote systems) via the cloud-based application. In some examples, the cloud-based application can communicate with an order management system to allow the user to order medical supplies (e.g., for use with the dialysis machine) via the gateway device.

The gateway device can also include a speaker for providing spoken information to the user. For example, the speaker can provide spoken instructions, answers to questions, confirmation of received instructions, etc. The microphone together with the speaker allow the gateway device to provide two-way conversational capability (e.g., back and forth communication). Such two-way communication can be particularly useful in a home dialysis setting to allow patients to provide information to the dialysis machine when the user may have difficulty manually entering data (e.g., due to limited dexterity, arthritis, etc.) or may be in a compromised state (e.g., disoriented due to being awoken at night, unable to see due to darkness or glasses not being within reach, etc.).

Figure 1:
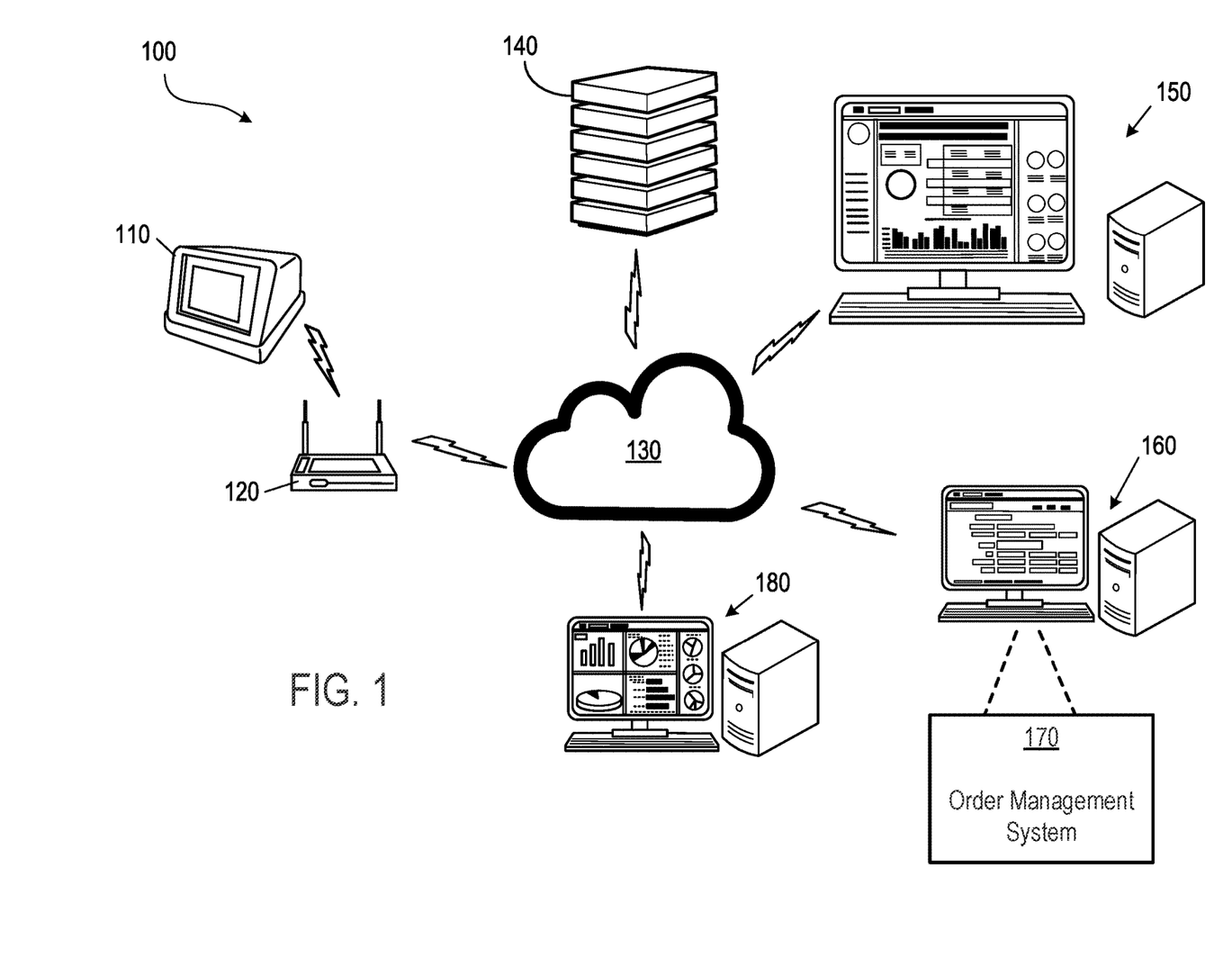
FIG. 1 is a schematic illustration showing an example of a Connected Health ("CH") system that includes a dialysis system and a gateway device.

FIG. 1 is a schematic illustration showing an example of a Connected Health ("CH") system 100 that includes, among other things, a dialysis system 110 (e.g., a home dialysis system), a gateway device 120 (e.g., a home gateway device), and a CH cloud 130 (e.g., a cloud server). The CH cloud 130 may be connected to the Internet. In some implementations, the gateway device 120 and the CH cloud 130 may be collectively referred to by the name "Reciprocity." The gateway device 120 is configured to receive data from the dialysis system 110 and provide the data to the CH cloud 130, and receive data from the CH cloud 130 and provide the data to the dialysis system 110. The dialysis system 110 and the gateway device 120 may communicate via a wired (e.g., Ethernet) or wireless connection (e.g., WiFi, Bluetooth, etc.). The dialysis system 110 and the gateway device 120 may communicate with one or more additional systems via the CH cloud 130. The CH cloud 130 may be a remote computing device, such as a server. In some implementations, the CH cloud 130 may be a cloud-based application that serves as a communication pipeline (e.g., facilitates the transfer of data) among components and systems of the CH system 100.

The CH system 100 includes one or more additional systems in communication with the CH cloud 130. In the illustrated example, the CH system 100 includes a prescription management system 140, a clinical information system 150, an operations system 160 that includes an order management system 170, and a technical support system 180.

The prescription management system 140 and/or the clinical information system 150 is configured to facilitate the transfer of medical prescriptions to/from the dialysis system 110 via the CH cloud 130 (e.g., via the gateway device 120). The prescriptions may be transferred between the prescription management system 140 and the clinical information system 150. The prescription management system 140 may be configured to examine compatibility of the prescription relative to the operational capabilities of the dialysis system 110 of the patient. The prescription management system 140 may facilitate entry of prescription data into the clinical information system 150 by a medical professional (e.g., a clinician or doctor), and may enable the clinical information system 150 to provide prescription parameters to one or more of the components and systems of the CH system 100. In some implementations, the prescription management system 140 and/or the prescription compatibility functionality of the prescription management system 140 may be referred to by the name "Unity."

In some implementations, the clinical information system 150 is located in a clinical setting (e.g., at a clinic, hospital, etc.). The clinical information system 150 is configured to store electronic health records of patients. The electronic health records can be examined by a medical professional to manage treatment of patients. Following a treatment provided by the dialysis system 110, the dialysis system 110 (e.g., via the gateway 120) may provide treatment data and/or patient data to the clinical information system 150 via the CH cloud 130 for storage. Such treatment data and/or patient data may be considered by a medical professional when generating a prescription using the prescription management system 140 and/or the clinical information system 150.

The operations system 160 is configured to perform activation/deactivation functions for the components of the CH system 100, manage supply chain (e.g., of medical supplies), and perform asset tracking functions. In particular, a primary function of the operations system 160 is to manage the ordering of medical supplies for a patient of the dialysis system 110. In the illustrated example, the operations system 160 includes the order management system 170, which is configured to receive orders from the patient of the dialysis system 110, provide order confirmation to the patient, monitor usage and inventory of medical supplies, and/or provide order recommendations, as described in more detail below. In some implementations, the order management system 170 may be provided as a separate system of the CH system 100 (e.g., separate from the operations system 160).

The technical support system 180 is configured to receive diagnostic information from the components and systems of the CH system 100. Technical support professionals can review such diagnostic information and use the technical support system 180 to issue commands and/or operations to the components and systems of the CH system 100. In this way, the technical support system 180 can be used for corrective action functions.

Figure 2:
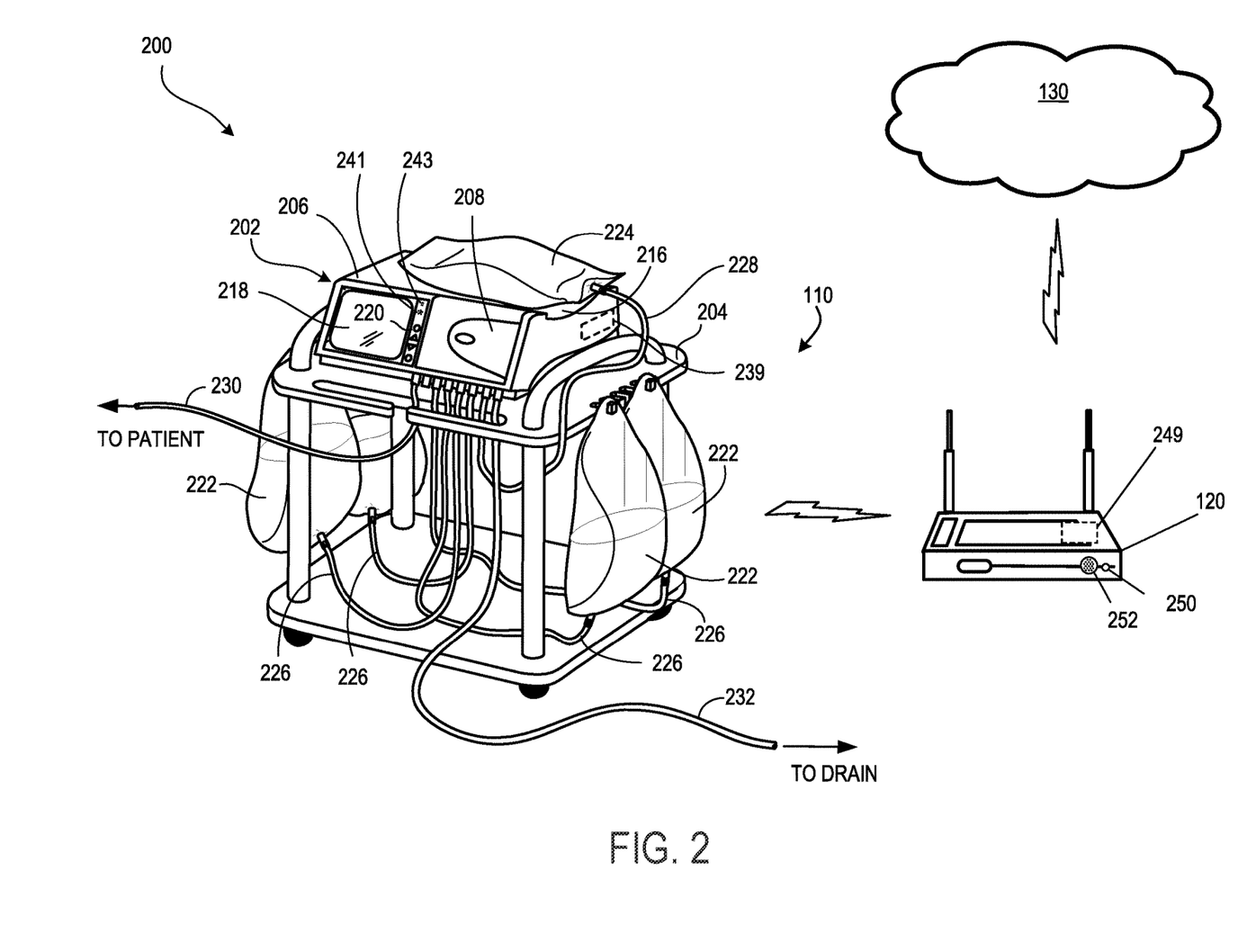
FIG. 2 shows an example of a system that includes the dialysis system and the gateway device of FIG. 1.

FIG. 2 shows an example of a system 200 that includes the dialysis system 110 and the gateway device 120 in communication with the CH cloud 130 of FIG. 1. In some implementations, the gateway device 120 itself is part of the dialysis system 110. For example, when the gateway device 120 is in communication with the dialysis system 110, or when the gateway device 120 becomes associated with the dialysis system 110 (e.g., when the gateway device 120 is first connected to the dialysis system 110), the gateway device 120 becomes part of the dialysis system 110 and is generally referred to as "belonging" to the dialysis system 110.

In some implementations, the dialysis system 110 is a home dialysis system. In the illustrated example, the dialysis system 110 is a peritoneal dialysis ("PD") system 110 that is configured for use in a home of a patient. It is noted that the PD system 110 is shown representationally and that other types and configurations of PD systems different than that principally described herein may be used in connection with the system described herein. The PD system 110 includes a PD machine (also referred to as a PD cycler) 202 seated on a cart 204. The PD machine 202 includes a housing 206, a door 208, and a cassette interface that contacts a disposable PD cassette when the cassette is disposed within a cassette compartment formed between the cassette interface and the closed door 208. A heater tray 216 is positioned on top of the housing 206. The heater tray 216 is sized and shaped to accommodate a bag of dialysate (e.g., a 5-liter bag of dialysate). The PD machine 202 also includes a user interface such as a touch screen display 218 and additional control buttons 220 that can be operated by a user (e.g., a caregiver or a patient) to allow, for example, set up, initiation, and/or termination of a PD treatment, as well as the medical supply ordering functions described below.

Dialysate bags 222 are suspended from fingers on the sides of the cart 204, and a heater bag 224 is positioned in the heater tray 216. The dialysate bags 222 and the heater bag 224 are connected to the cassette via dialysate bag lines 226 and a heater bag line 228, respectively. The dialysate bag lines 226 can be used to pass dialysate from dialysate bags 222 to the cassette during use, and the heater bag line 228 can be used to pass dialysate back and forth between the cassette and the heater bag 224 during use. In addition, a patient line 230 and a drain line 232 are connected to the cassette. The patient line 230 can be connected to a patient's abdomen via a catheter and can be used to pass dialysate back and forth between the cassette and the patient's peritoneal cavity during use. The drain line 232 can be connected to a drain or drain receptacle and can be used to pass dialysate from the cassette to the drain or drain receptacle during use.

The PD machine 202 also includes a control unit 239 (e.g., a processor) that is configured to receive signals from and transmit signals to the touch screen display 118, the control panel 120, and the various other components of the PD system 110 and/or the gateway device 120. The control unit 239 is configured to control operating parameters of the PD machine 202.

The gateway device 120 is configured to communicate with the PD machine 202. In this way, the gateway device 120 can act as a communications hub (e.g., node) that allows communication between the PD machine 202 and one or more other systems and/or devices. While the gateway device 120 is in wireless communication with the PD machine 202 in the illustrated example, the gateway device 120 and the PD machine 202 may also or alternatively be connected by a wired connection (e.g., an Ethernet cable). The gateway device 120 includes a control unit 249 (e.g., a processor), a microphone 250, and a speaker 252. The gateway device 120 is configured to receive audio input (e.g., spoken words, such as commands, questions/answers, etc.) through the microphone 250 and provide audio output (e.g., spoken words, such as questions/answers, instructions, alarms, alerts, confirmations, etc.) through the speaker 252. The control unit 249 is configured to process the audio input received through the microphone 250 and identify the spoken words. For example, the control unit 249 may include voice recognition capability that allows the control unit 249 to convert the audio input into words of a spoken language. The control unit 249 can identify questions, answers, commands, etc. formed by the recognized words.

In some implementations, the processing unit 249 may provide identified questions, answers, commands, etc. to the CH cloud 130 for remote processing. The CH cloud 130 may then provide data to the processing unit 249 that allows the processing unit 249 to cause the speaker 252 to output the audio output. For example, the CH cloud 130 may provide the identified spoken words to one or more other systems (e.g., the order management system 170 of FIG. 1, among others), where the spoken words are processed to obtain a result (e.g., an answer to a question, a follow up question, an instruction, etc.). The CH cloud 130 can receive data indicative of the result, and provide data to the processing unit 249 that the processing unit 249 uses to cause the speaker 252 to output spoken words indicative of the result. Similarly, in some implementations, the processing unit 249 may provide commands directly to the PD machine 202 for processing by the control unit 239 of the PD machine 202. The PD machine 202 may control one or more operating parameters of the PD machine 202 based on the commands.

In some implementation, the microphone 250 is configured to receive audio information (e.g., spoken information) as input from a user, such as a patient or a caregiver. The processing unit 249 can receive the audio information from the microphone 250 and identify one or more voice commands, questions, answers, etc. in the audio information. In some implementations, an audio message is presented by the speaker 252 if the spoken information is not understood or not permitted. For example, the speaker 252 may prompt the user to repeat himself or herself, or ask the user for clarification regarding the spoken information. In some implementations, the processing unit 249 is configured to translate the audio information into text (e.g., for providing to the CH cloud 130 and/or the PD machine 202. In some implementations, the processing unit 249 is configured to cause the PD machine 202 to perform an action based on one or more spoken words identified in the audio information.

In some implementations, the spoken words cause the PD machine 202 to perform a dialysis action (e.g., a dialysis function, a dialysis treatment function, etc.). Such dialysis actions can cause the PD machine 202 to set and/or modify one or more parameters used for carrying out a treatment for a patient (e.g., the user). In some examples, the text that is translated based on the audio information is compared to information stored on the gateway device 120, the PD machine 202, etc., such as stored text, that corresponds to known voice commands, questions, and answers. For example, the processing unit 249 may translate audio information into a text string "set dialysate flow rate to 500 milliliters per minute." Information stored on the gateway device 120 and/or the PD machine 202 may include the text string "set dialysate flow rate" and information linking the text string to a "set dialysate flow rate" voice command. The spoken text string is compared to the stored text string, and based on the comparison, invocation of the "set dialysate flow rate" voice command is identified. The control unit 249 can then provide instructions for causing the PD machine 202 to carry out a function related to the voice command. The text to which the translated text is compared may be stored on the PD machine 202, the gateway device 120, and/or at another location accessible by the PD system 110 (e.g., on a server, in a database, etc. accessible by the CH cloud 130).

In some implementations, the voice recognition capabilities of the gateway device 120 may allow the user to enter data into the PD machine 202. Such voice-based data entry can be used instead of or in addition to manual data entry via the touch screen display 218. For example, during a set-up of the PD machine 202, the user may be prompted by the touch screen display 218 to enter various patient information, such as a name, identification number, weight, prescription information, etc. In some implementations, the user may interact with an input field that corresponds to a particular parameter (e.g., a name field) on the touch screen display 218 to cause the field to be selected. Thereafter, the microphone 250 of the gateway device 120 may expect a voice input from the user. The user can speak his or her name aloud, the microphone 250 can receive the audio input, the control unit 249 can convert the audio input to spoken words, and the spoken words can be provided to the PD machine 202. The spoken words identified by the gateway device 120 can be provided on the touch screen display 218 in the name field. If the presented name is incorrect, the user can speak a command to edit the presented name. For example, take an example in which the user selects the name field, speaks "Bryan" aloud, and the name field displays "Brian." The user may say, "Change the 'i' to a 'y'" to cause the presented name to update to the correct name. In some implementations (e.g., implementations in which incorrect words are identified and presented), the user may provide an undo or repeat voice command to cause the touch screen display 218 to remove the incorrect information and prompt the microphone 250 to expect new audio input.

In some implementations, the gateway device 120 may provide information related to the one or more spoken words identified in the audio information to one or more systems and/or devices (e.g., remote systems and/or devices) via the CH cloud 130, and the one or more systems and/or devices may assist in determining an action to be performed based on the identified spoken words. For example, the gateway device 120 may provide the information related to the one or more spoken words to the prescription management system 140, the clinical information system 150, the operations system 160, the order management system 170, and/or the technical support system 180.

In some implementations, the gateway device 120 may provide two-way conversational capability (e.g., back and forth communication) between the user and the gateway device 120. That is, the gateway device 120 may be configured to identify spoken words from the user, generate a spoken response based on the identified spoken words, receive a spoken response from the user, etc., in which each step of the spoken transaction is intelligently determined (e.g., by the gateway device 120 and/or one or more other devices/systems) based at least one previous spoken information. For example, take an example in which the user select a weight field on the touch screen display 218. The speaker 252 of the gateway device 120 may ask, "What is your weight today?" The microphone 250 of the gateway device 120 may then expect audio input. The user can respond, for example, "My weight is 150 pounds." The gateway device 120 may then confirm that the audio input was correctly identified before inputting the weight in the weight field. For example, the speaker 252 may ask, "OK, I have 150 pounds for your weight, is that correct?" The user can respond, "Yes," and a weight of 150 pounds can be entered into the weight field.

In some implementations, during set-up of the PD machine 202, each of various patient input parameters may be automatically stepped through in a manner similar to that described above. In other words, in some examples, the user need not first make a selection on the touch screen display 218 to initiate voice data entry. Rather, the gateway device 120 may ask the user to enter a first element of patient information via a first spoken question, cause the first element of patient information to be entered into the PD machine 202, ask the user to enter a second element of patient information via a second spoken question, cause the second element of patient information to be entered into the PD machine 202, etc. In some implementations, each element of patient information is confirmed with the user (e.g., via a follow-up confirmation question, a message/input via the touch screen display 218, etc.) before the element of patient information is input into the PD machine 202. Such data entry can allow for simple data entry for all types of users, such as users who have difficulty seeing/reading the touch screen display 218, users who have difficulty manually inputting data into the touch screen display 218, users who are unprepared or unfit to manually input data (e.g., users who are disoriented due to being awoken in the middle of the night, unable to see due to dark lighting conditions or not having glasses available, etc.).

In some implementations, the gateway device 120 may provide data to the user using the speaker 252 (e.g., independent of the follow-up/confirmation questions described above). For example, data that may be provided by the touch screen display 218 of the PD machine 202 may also, or alternatively, be provided to the user in the form of spoken words. In some examples, the user may ask the gateway device 120 to cause some or all of the information displayed by the touch screen display 218 of the PD machine 202 to be audibly provided as spoken words via the speaker 252 of the gateway device 120. In some implementations, the gateway device 120 may be configured to identify particular questions and provide requested information as spoken words in response. For example, the user can ask, "How much longer for my treatment," and the speaker 252 can answer, "There are 35 minutes remaining in the treatment."

Figure 3:
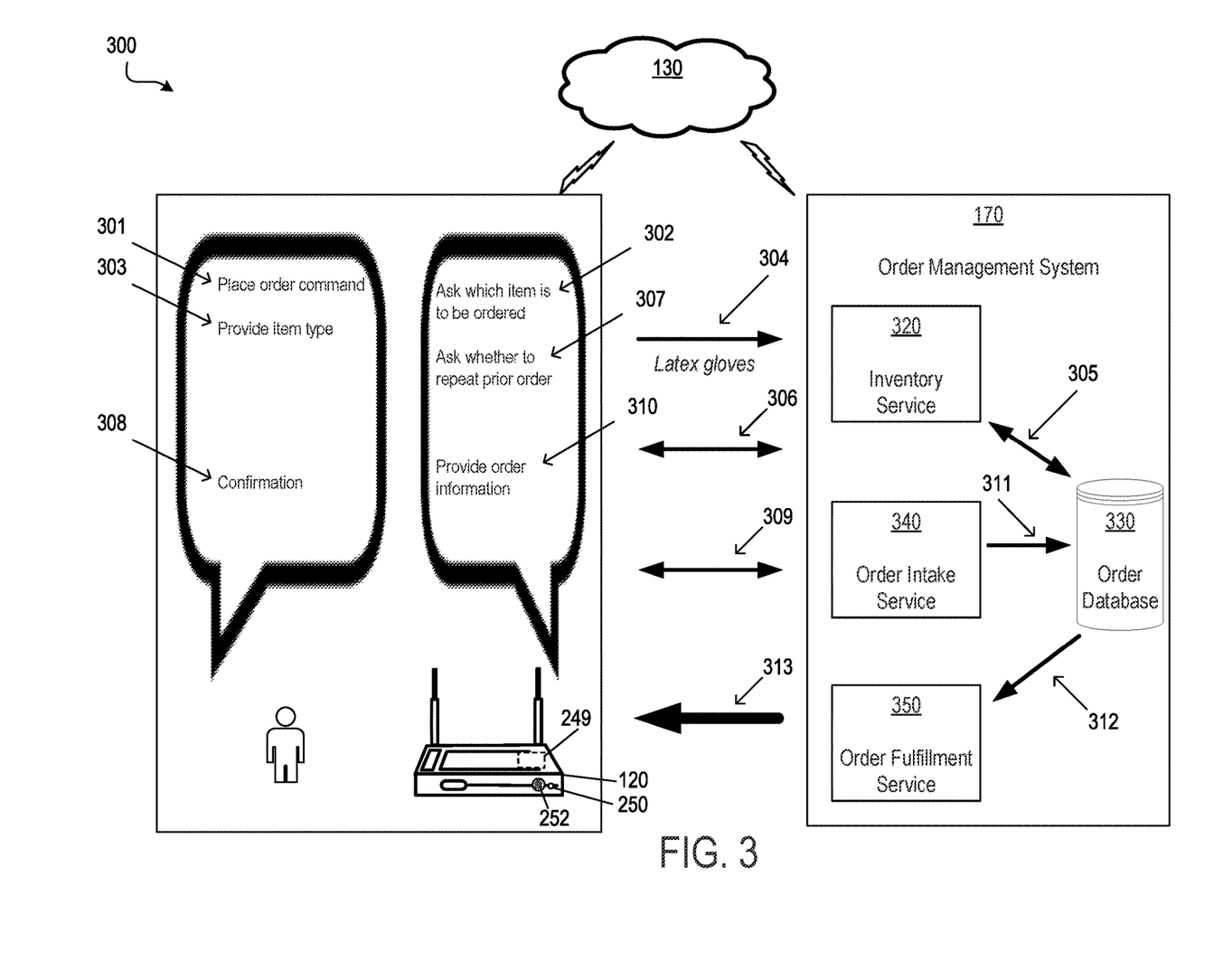
FIG. 3 shows an example of a communication workflow that illustrates a voice-based ordering technique facilitated by the gateway device of FIGS. 1 and 2.

In some implementations, the gateway device 120 is configured to communicate with the order management system (170 of FIG. 1) to allow a user to order medical supplies using spoken information. FIG. 3 shows an example of a communication workflow 300 that illustrates a voice-based ordering technique facilitated by the gateway device 120. At 301, a request to place an order (e.g., a place order command) is received by the gateway device 120. For example, a user (e.g., a patient) of the PD system 110 may say, "I would like to place an order." The microphone 250 of the gateway device 120 receives the spoken information as audio input, and the control unit 249 processes the audio input to identify spoken words. Based on the identified spoken words, the gateway device 120 identifies that the place order command 501 has been implemented.

At 302, the gateway device 120 asks which item (e.g., medical item) is to be ordered. For example, the speaker 252 of the gateway device 120 may say, "What would you like to order?"

At 303, the user provides an item type. For example, the user may say, "Order latex gloves." The microphone 250 of the gateway device 120 receives the spoken information as audio input, and the control unit 249 processes the audio input to identify spoken words.

At 304, information (e.g., text) indicative of the identified spoken words is provided to the order management system 170 via the CH cloud 130. At the order management system 170, an inventory service 320 is queried based on the identified item. In particular, the inventory service 320 determine ordering trends of the patient for the identified item.

At 305, the inventory service 320 communicates with an order database 330 to identify past orders placed by the user for the identified item. The order database 330 may include orders placed by various users over a particular amount of time. The inventory service 320 may identify a recent (e.g., a most recent) order placed for the identified item. In this example, the inventory service 320 may identify an order in the order database 330 for one box of latex gloves that was placed one month prior.

At 306, the inventory service 320 communicates information to the gateway device 120 indicative of the recent order placed by the user. For example, the inventory service 320 may indicate to the gateway device 120 that the user placed an order for one box of latex gloves one month prior, and may also provide a date at which the order was placed.

At 307, the speaker 252 of the gateway device 120 asks whether to repeat the prior order. For example, the speaker 252 may say, "An order for one box of latex gloves was placed one month ago. Would you like to repeat that order?" In some implementations, the date at which the prior order was placed may also be provided by the speaker 252. In some implementations, one or more modifications to the prior order may be recommended by the order management system 170, and the modified order may be provided by the gateway device 120, as described in more detail below.

In some implementations, rather than the gateway device 120 asking whether to repeat a prior order, the order management system 170 may recommend a different order for consideration by the user. For example, the order management system 170 may recommend that a new order be placed (e.g., an order that has not previously been placed). The recommendation may be based on information received from the inventory service 320. In some implementations, rather than recommending that the particular quantity of the item from a previous order be placed, the order management system 170 may recommend an alternative quantity. Such a recommendation may be based on an expected local inventory of the item (e.g., at the location of the PD machine 202) and/or a known or expected rate of consumption of the item.

At 308, the user provides confirmation that the prior order should be repeated. For example, the user may say, "Yes" in response to the query from the gateway device 120. The microphone 250 of the gateway device 120 receives the confirmation to repeat the prior order. In some implementations, the user may be prompted to provide a passcode before the order is accepted by the gateway device 120. The passcode may be provided via the touch screen display 218 of the PD machine 202 or verbally via the microphone 250 of the gateway device 120.

Alternatively, the user may indicate that he or she would not like to repeat the prior order, for example, by saying "No." In such a case, the order management system 170 may provide a different order to the gateway device 120, and the gateway device 120 may ask the user whether the different order should be repeated, or the gateway device 120 may cancel the ordering process.

At 309, the gateway device 120 provides the confirmation to repeat the prior order to an order intake service 340 of the order management system 170. The order intake service 340 indicates to the gateway device 120 that the order was accepted, and provides order information to the gateway device 120. For example, the order intake service 340 may provide a confirmation number for the order, an expected date of shipment of the order, an expected date of receipt of the item, etc.

At 310, the speaker 252 of the gateway device 120 provides the order information to the user. For example, the speaker 252 may say, "Order placed. Expected delivery is next Tuesday. Confirmation Number is '12ABC3.'" In some implementations, if the user identifies incorrect information in the order information, the user may respond to the gateway device 120 with spoken instruction to cancel the order or modify the order to correct such inaccuracies.

At 311, the order intake service 340 processes the order and provides information related to the placed order to the order database 330 for storage. For example, the name of the user, a shipping address of the user, the item type, the item quantity, the order date, the expected shipping date, the expected delivery date, the confirmation number, etc. can be provided to the order database 330 for storage. Such order information can be included in the order history that is considered for future orders (e.g., for repeat orders, recommended orders, etc.).

At 312, an order fulfillment service 350 receives the information related to the order from the order database 330 and causes the order to be prepared for shipment. For example, the order fulfillment service 350 may receive information such as the name of the user, the shipping address of the user, the item type, the item quantity, etc. Preparing the order for shipment may include sending one or more communications (e.g., to personnel in communication with the order fulfillment service 350) to cause the item type and quantity to be gathered and packaged. In some implementations, the order fulfillment service 350 may communicate with one or more other entities to facilitate fulfillment of the order. For example, the information related to the order may be provided to a third party, and the third part may assist in performing one or more parts of the order fulfillment process.

At 313, the order fulfillment service 350 causes the order to be shipped to the user. For example, the order, which had been prepared for shipment, may be provided to a shipping service, and the shipping service provides the order to the shipping address of the user.

In some implementations, the gateway device 120 is configured to allow the user to check a status of the order. For example, the user may say, "What is the status of my order?" The microphone 250 of the gateway device 120 receives the spoken information as audio input, and the control unit 249 processes the audio input to identify spoken words (e.g., the request for a status update). The request for the status update is provided to the order management system 170 via the CH cloud 130, the order management system 170 checks the status of the order (e.g., by querying one or more components and/or external systems), and information related to the status of the order is provided to the gateway device 120 via the CH cloud 130. The gateway device 120 then causes the speaker 252 to provide a spoken message providing the order. For example, the gateway device 120 may say, "Your order for one box of latex gloves is scheduled to arrive tomorrow."

Figure 4:
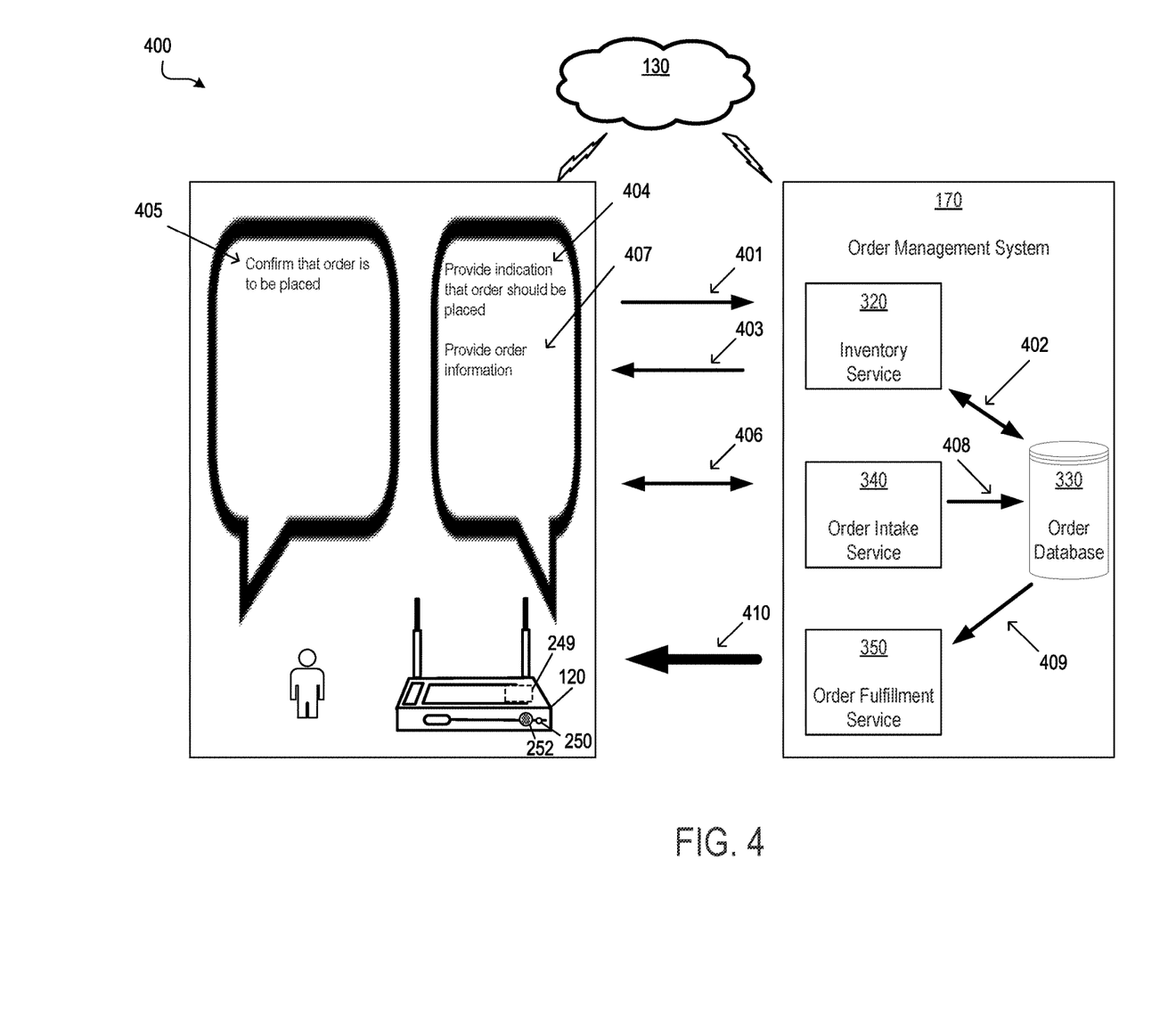
FIG. 4 shows an example of a communication workflow that illustrates a voice-based ordering technique initiated by the gateway device of FIGS. 1 and 2.

FIG. 3 described an implementation in which an order for medical supplies is initiated by the user (e.g., by the user issuing a place order command at 301). In some implementations, the gateway 120 and/or the order management system 170 may initiate the order (e.g., a proposed order). FIG. 4 shows an example of a communication workflow 400 that illustrates a voice-based ordering technique initiated by the gateway device 120. At 401, the gateway device 120 communicates with the inventory service 320 to determine an estimated local inventory (e.g., at the location of the PD machine 202) of a particular item. For example, the gateway device 120 may make a service call to the inventory service 320 via the CH cloud 130.

In some implementations, the gateway device 120 may initiate an inventory check for a particular item at a predetermined frequency (e.g., once a day, once a week, etc.). In some implementations, the predetermined frequency may be based on the particular item and/or a relative importance of the particular item. For example, items that are essential for treatment may be checked once a day (or more), and optional/ancillary items may be checked at a lesser frequency (e.g., once a week, once a month, etc.).

At 402, the inventory service 320 communicates with the order database 330 to collect information related to previous orders placed by the user. For example, the inventory service 320 may receive information from the order database 330 related to a quantity of the item previously ordered, a date at which previous orders were placed, etc. Such information is used to determine an estimated local inventory of the item at the location of the PD machine 202 (e.g., at the home of the patient). In some implementations, the inventory service 320 may provide the estimated local inventory, for example, by identifying a quantity of the most recent order for the item, identifying an expected or known consumption rate of the item, and identifying a length of time that has elapsed between the date of the most recent order and the current date.

At 403, the inventory service 320 provides the information related to the previous orders to the gateway device 120. For example, the inventory service 320 may return the quantity of the item previously ordered, a date at which previous orders were placed, etc. to the gateway device 120, and the gateway device 120 determines the estimated local inventory of the item. In some implementations, the inventory service 320 determines the estimated local inventory of the item and provides the estimated local inventory of the item to the gateway device 120.

The gateway device 120 determines, based on the estimated local inventory of the item, whether there is a current or anticipated shortage of supply for the item. For example, the gateway device 120 may compare the estimated local inventory of the item (e.g., as provided by the inventory service 320 or as determined based on information provided by the inventory service 320) to locally stored information related to the consumption (e.g., actual consumption) of the item to determine whether there is a current or anticipated shortage of supply.

In some implementations, a rules based engine may determine whether there is a current or anticipated shortage of supply. The rules based engine may be local to the gateway device 120 (e.g., incorporated into software operating on the gateway device 120). For example, the rules based engine may determine the consumption of the item based on information local to the gateway device 120 and/or the PD machine 202. In some examples, the user may provide an indication to the PD machine 202 and/or the gateway device 120 when a particular item is used. Such indications may be provided via voice input through the gateway device 120, through the touch screen display 218 of the PD machine 202, etc. The rules based engine may use such information to determine the actual inventory of the item at the home of the patient. In some implementations, if the actual inventory of the item is less than the estimated local inventory, an indication may be provided to the user that an order should be placed, as described in more detail below.

In some implementations, the rules based engine is part of the order management system 170. For example, the rules based engine at the order management system may determine whether there is a current or anticipated shortage of supply. Such a determination may be made based at least in part on information related to an actual inventory of the item received from the gateway device 120. In some implementations, the information related to the actual inventory of the item may be present at the order management system 170. For example, such information may be previously provided by the gateway device 120 or determined by other means (e.g., by communication with one or more other systems and/or devices via the CH cloud 120).

In some implementations, the rules based engine can determine whether there is a current or anticipated shortage of supply of the item based on the actual local inventory of the item and a known or expected consumption rate of the item (e.g., including an expected frequency of treatments provided by the PD machine 202). In some implementations, additional information is also taken into account, such as a known or expected availability of the item, an expected delay in shipping of the item, a duration required to ship the item, etc. For example, the rules based engine may determine that a particular item (e.g., latex gloves) are used once per day for the user, and that the user currently has seven pairs of latex gloves remaining. Thus, the rules based engine determines that the user has seven days' worth of supply remaining. The rules based engine may identify that five days are required between placing an order for latex gloves and receipt of the order at the home of the user. Therefore, the rules based engine may determine that an order for latex gloves should be placed within two days to avoid the user running out of supply. In some implementations, if the estimated length of time required for ordering the item to avoid running out of supply is less than a predetermined threshold (e.g., a week), an indication may be provided to the user that an order should be placed.

At 404, if the rules based engine determines that an order should be placed for the item to avoid running out of supply, the gateway device 120 provides an indication to the user that an order should be placed (e.g. a recommendation to place an order). For example, the gateway device 120 may say, "It looks like you are running low on latex gloves. Would you like to place a refill order?" In some implementations, the indication may include additional information, such as the determined inventory of the item, an expected length of time before the user runs out of the item, an expected length of time between placing an order and receipt of the shipment, etc. In some implementations, the indication may include a specific recommendation for an order to be placed. For example, the gateway device 120 may provide a recommended quantity of the item for the order, a length of time that such a quantity of the item is expected to last, etc.

At 405, the user confirms that the order is to be placed. For example, the user may simply say, "Yes," or "Place the order." In some implementations, the user may be prompted to provide a passcode before the order is accepted by the gateway device 120. The passcode may be provided via the touch screen display 218 of the PD machine 202 or verbally via the microphone 250 of the gateway device 120.

Alternatively, the user may indicate that he or she would not like to place the recommended order, for example, by saying "No." In such a case, the order management system 170 may provide a different recommended order to the gateway device 120, and the gateway device 120 may ask the user whether the different order should be repeated, or the gateway device 120 may cancel the ordering process. In some implementations, the user may provide a modification to the recommended order, such as a modified quantity, and the modified order may proceed according to the workflow 400.

At 406, the gateway device 120 provides confirmation that the order is to be placed to the order intake service 340 of the order management system 170. The order intake service 340 indicates to the gateway device 120 that the order was accepted, and provides order information to the gateway device 120. For example, the order intake service 340 may provide a confirmation number for the order, an expected date of shipment of the order, an expected date of receipt of the item, etc.

At 407, the gateway device 120 provides the order information to the user. For example, the speaker 252 may say, "Order placed. Expected delivery is next Friday. Confirmation Number is '32BAC1.'" In some implementations, if the user identifies incorrect information in the order information, the user may respond to the gateway device 120 with spoken instruction to cancel the order or modify the order to correct such inaccuracies.

At 408, the order intake service 340 processes the order and provides information related to the placed order to the order database 330 for storage. For example, the name of the user, a shipping address of the user, the item type, the item quantity, the order date, the expected shipping date, the expected delivery date, the confirmation number, etc. can be provided to the order database 330 for storage. Such order information can be included in the order history that is considered for future orders (e.g., for repeat orders, recommended orders, etc.).

At 409, the order fulfillment service 350 receives the information related to the order from the order database 330 and causes the order to be prepared for shipment. For example, the order fulfillment service 350 may receive information such as the name of the user, the shipping address of the user, the item type, the item quantity, etc. Preparing the order for shipment may include sending one or more communications (e.g., to personnel in communication with the order fulfillment service 350) to cause the item type and quantity to be gathered and packaged. In some implementations, the order fulfillment service 350 may communicate with one or more other entities to facilitate fulfillment of the order. For example, the information related to the order may be provided to a third party, and the third part may assist in performing one or more parts of the order fulfillment process.

At 410, the order fulfillment service 350 causes the order to be shipped to the user. For example, the order, which had been prepared for shipment, may be provided to a shipping service, and the shipping service provides the order to the shipping address of the user. The gateway device 120 is also configured to allow the user to check a status of the order, as described above.

While certain implementations have been described, other implementations are possible.

While various questions, answers, and commands have been described as being recognizable by the voice recognition systems and techniques described herein, other voice recognition capabilities are also possible. Examples of voice recognition functionality that may be incorporated into the systems and techniques described herein are disclosed in U.S. Pat. No. 9,839,735, entitled "VOICE INTERFACE FOR A DIALYSIS MACHINE," the entire contents of which are hereby incorporated by reference.

In some implementations, the voice recognition systems and techniques described herein may be configured to support appointment scheduling functions. The microphone may be configured to receive audio information from the user that includes a command to schedule an appointment. The processing unit can receive the audio information (e.g., spoken information) and identify the appointment scheduling command in the audio information. For example, the user may say, "Schedule a dialysis appointment for Feb. 15, 2018, at 1:00 PM". The processing unit can translate the spoken information into text, and the translated text can be compared to stored information (e.g., stored text) that corresponds to known voice commands. The appointment scheduling command may be identified, and an appointment scheduling function may be invoked by the system. In some examples, the appointment scheduling function may invoke one or more systems of the CH system.

In some examples, the system may determine whether the date and time provided by the user is available. If the date and time for the appointment is available, the system may provide feedback to the user confirming the appointment. For example, the speaker may confirm, "An appointment has been scheduled for Feb. 15, 2018 at 1:00 PM." In some implementations, the user may provide additional information in the appointment request, such as a requested medical professional for the appointment. Such additional information can be compared to a schedule of the medical professional to determine whether the requested date and time is available.

In some implementations, the system may also be configured to allow the user to request information related to scheduled appointments. For example, the user may say, "When is my next appointment?," and the speaker can respond, "Your next appointment is scheduled for next Tuesday, Dec. 12, 2017, at 2:00 PM with Doctor Miller."

In some implementations, the voice recognition systems and techniques described herein may be configured to support ride scheduling functions. For example, the user may say, "Schedule a ride to my appointment for Dec. 12, 2017, at 2:00 PM." The system can determine whether a transportation service is available for the requested time. For example, the system may communicate with a transportation service associated with the medical facility where the appointment is to take place, and/or a third party transportation service (e.g., a ride sharing service, public transportation, etc.). Upon identifying an available transportation service, the system can confirm that the requested ride has been scheduled by causing the speaker to respond, "Your requested ride for Dec. 12, 2017, at 2:00 PM, has been scheduled." In some implementations, the confirmation can include information related to the transportation service that is to provide the ride. For example, the confirmation can include a time at which the transportation service is to arrive at the location of the user, a location where the transportation service is to pick up the user, etc. In some implementations, the system may also be configured to provide the status of scheduled rides to the user upon request.

In some implementations, the voice recognition systems and techniques described herein may be configured to support user requests for information related to treatments, patient conditions, patient data, etc. For example, the user may say, "When was my last treatment," and the speaker may respond, "Your last treatment was on Monday, and your next treatment is scheduled for Thursday." The user may ask how long a previous treatment lasted, and the system can respond with the length of the previous treatment. The user may ask what his or her weight was at the time of the previous treatment and/or an average weight over a particular time span, and the system can respond with the weight at the time of the previous treatment and/or the average weight over the time span. The user can ask if any errors occurred during a previous treatment, data related to the previous treatment, etc., and the system can respond accordingly. With each of the above-mentioned functions, the system may communicate with one or more of the systems of the CH system to determine the requested information.

In some implementations, the voice recognition systems and techniques described herein may be configured to support requests for information related to received communications. For example, the system may be configured to receive messages from one or more entities (e.g., medical professionals). The system may be configured to allow the user to ask whether any messages have been received. In response, the system may read the message aloud. In some implementations, the system may be configured to read messages aloud without specifically being prompted. For example, the system may be configured to read message aloud upon receipt or in response to detecting that the user is proximate to the system (e.g., upon the user signing into the system).

In some implementations, the system may be configured to receive updates (e.g., software updates) for updating the functionality of the system (e.g., the dialysis system). The voice recognition systems and techniques described herein may be configured to support requests for updates. The user can ask the system whether any software updates are available, and the system can verbally identify available software updates. Upon further instruction from the user, the system may be configured to download and/or install such software updates.

Figure 5:
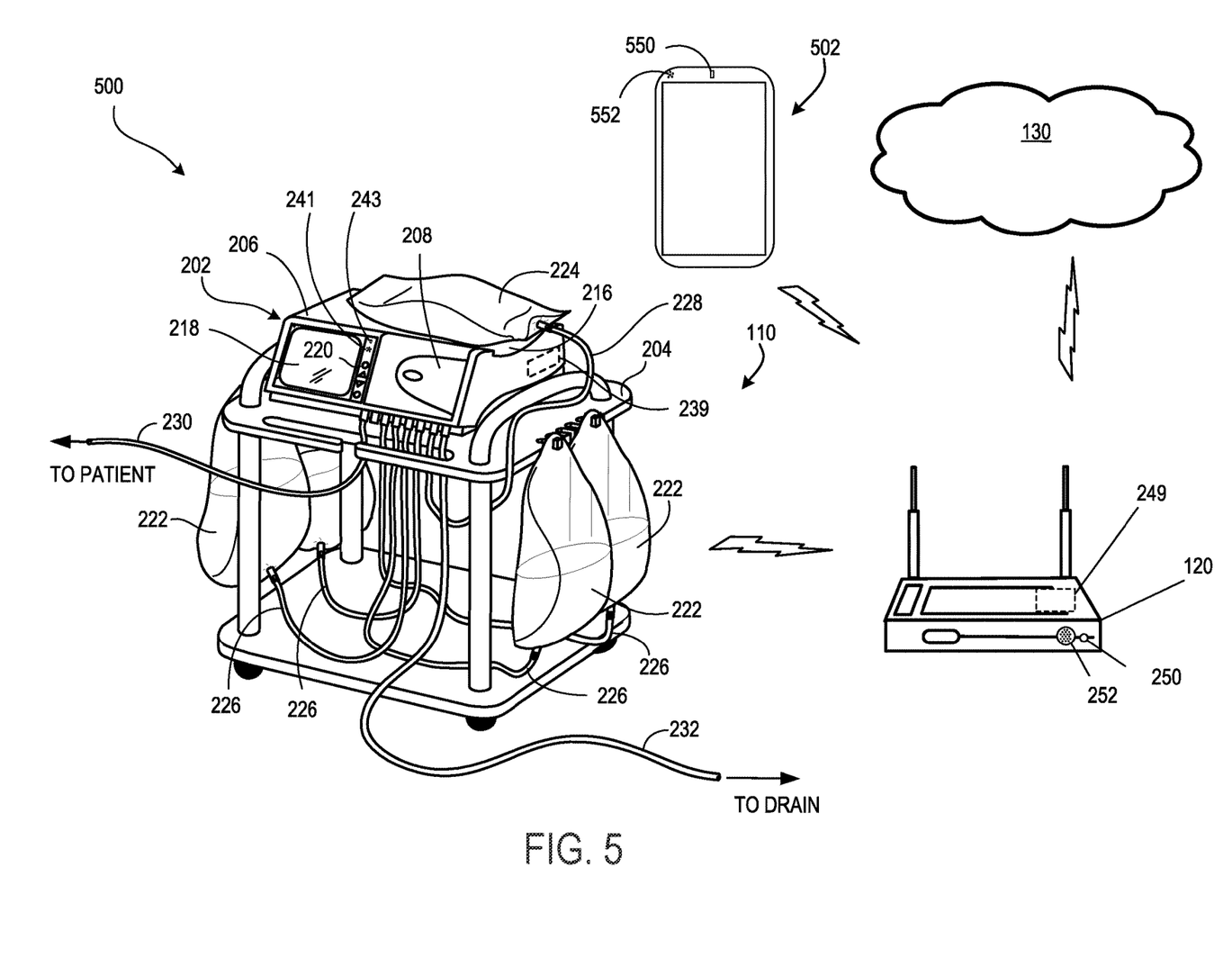
FIG. 5 shows an example of a system that includes a mobile computing device, and the dialysis system and the gateway device of FIG. 1.

While the microphone and the speaker have been described as being included as part of the gateway device, other implementations are possible. In some implementations, a separate, external electronic device also or alternatively include a microphone or a speaker. FIG. 5 shows an example of a system 500 that includes the PD system 110, the gateway device 120, and a mobile computing device 502. The mobile computing device 502 is in communication (e.g., wired or wireless communication) with one or more of the PD machine 202, the gateway device 120, and the CH cloud 130. In the illustrated example, the mobile computing device 502 is a mobile phone, but other mobile computing devices may also or alternatively be used, such tablet computers, laptop computers, personal digital assistants (PDAs), etc.

The mobile computing device 502 includes a microphone 550 and a speaker 552 and is configured to provide voice recognition capability substantially as described above. In some implementations, the gateway device 120 of the system 500 may omit its microphone 250 and/or speaker 252, and the voice recognition capabilities and two-way conversational capabilities may be handled by the mobile computing device 502 (e.g., an application running on the mobile computing device). In this way, the mobile computing device 502 may serve as a communication conduit between the PD machine 202 and the CH cloud 130, or between the PD machine 202, the gateway device 120, and/or the CH cloud 130.

While the dialysis system has been largely described as being a peritoneal dialysis (PD) system, and in particular as being a specific home PD system, other medical treatment systems can employ the techniques described herein.

Examples of other medical treatment systems include another type and/or configuration of PD system, hemodialysis (HD) systems, hemofiltration systems, hemodiafiltration systems, apheresis systems, and cardiopulmonary bypass systems, located at a patient's home or elsewhere.

While the microphone and the speaker have largely been described as being included as part of the gateway device, other implementations are possible. In some implementations, the dialysis machine itself may include the microphone and/or the speaker. The dialysis machine may be configured to identify spoken words in audio data received by the microphone, and provide audio output that includes spoken words via the speaker.

While the control unit of the gateway device has been largely described as including voice recognition capability, other implementations are possible. In some implementations, the microphone of the gateway device may receive raw audio data (e.g., audio data that is not yet recognized as including spoken words), and the raw audio data may be provided to the CH cloud and/or the dialysis machine for processing. Once received by the CH cloud (or, e.g., a system in communication with the CH cloud, such as the order processing system) or the dialysis machine, the raw audio data can be processed such that spoken words are identified. In this way, the voice recognition takes place at a device/system other than the gateway device.

With respect to the voice-based ordering techniques described above, while various commands are described as being identified by the gateway device 120, in some implementations, spoken information may be provided to the CH cloud, and the CH cloud may identify particular commands. For example, with respect to the place order command (301 of FIG. 1), the spoken words may be provided to the CH cloud, the CH cloud may identify the place order command, and the CH cloud may indicate to the gateway device that the place order command has been implemented, thereby causing the gateway device to ask which item is to be ordered.

While latex gloves were identified as being the particular medical supply ordered in the examples above, other supplies may also be ordered using the systems and techniques described herein. For example, items can include other types of medical supplies, such as medications, tubes/hoses for the dialysis machine, medical tools (e.g., surgical tools), dialysate, and/or dialysate components, to name just a few.

While the ordering techniques described above have been describes as optionally requiring confirmation from the user before the order is placed, in some implementations, an order may automatically be placed. For example, if the rules based engine identifies that an order should be placed, the order fulfillment service may automatically cause the ordered to be placed and shipped to the user.

Figure 6:
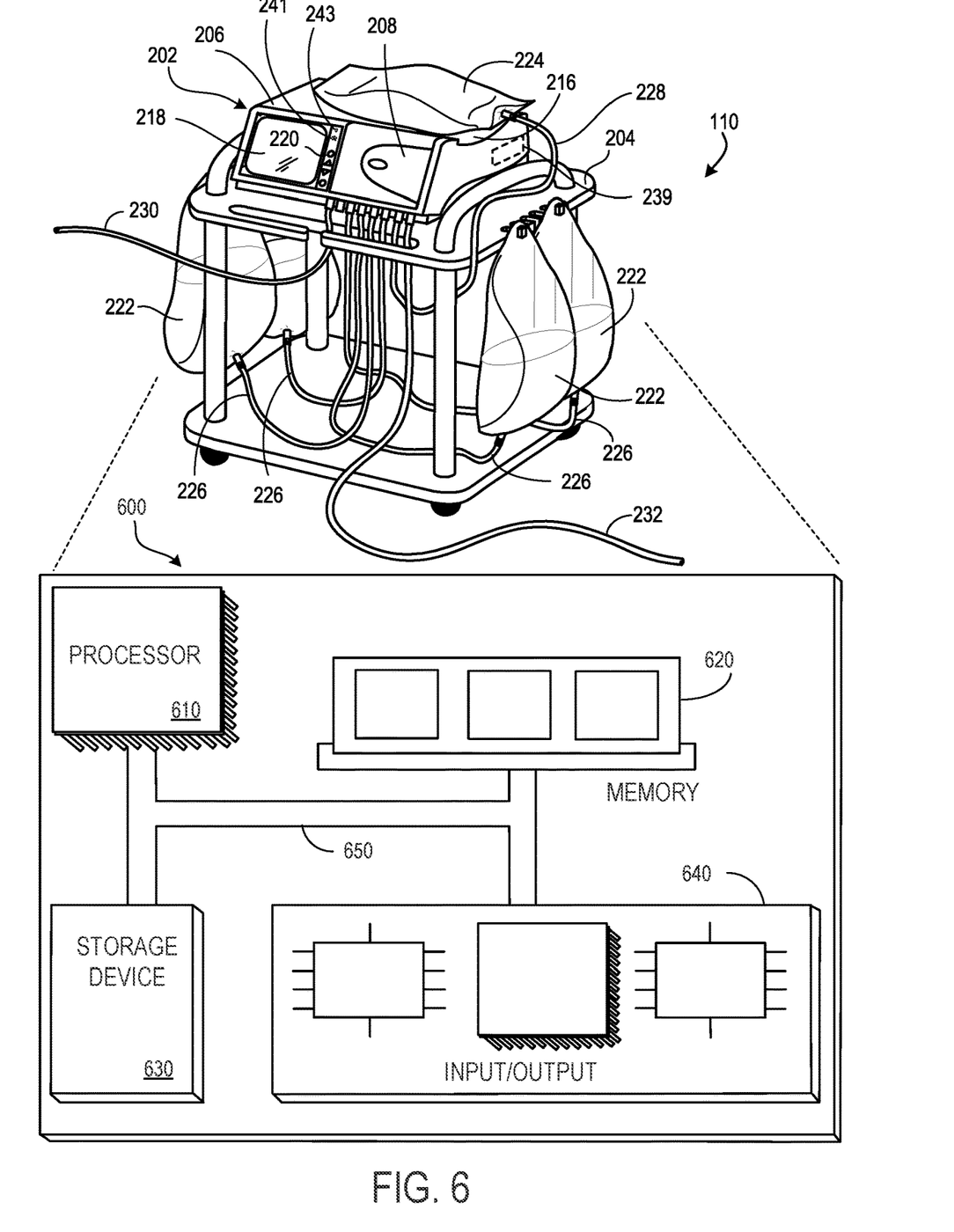
FIG. 6 shows an example of a computer system.

FIG. 6 is a block diagram of an example computer system 600. For example, the various electronic devices/systems described herein may be examples of, or may include one or more examples of, the system 600. The system 600 includes a processor 610, a memory 620, a storage device 630, and an input/output device 640. Each of the components 610, 620, 630, and 640 can be interconnected, for example, using a system bus 650. The processor 610 is capable of processing instructions for execution within the system 600. The processor 610 can be a single-threaded processor, a multi-threaded processor, or a quantum computer. The processor 610 is capable of processing instructions stored in the memory 620 or on the storage device 630. The processor 610 may execute operations such as causing the systems to carry out functions related to voice (e.g., non-touch) communication.

The memory 620 stores information within the system 6900. In some implementations, the memory 620 is a computer-readable medium. The memory 620 can, for example, be a volatile memory unit or a non-volatile memory unit.

The storage device 630 is capable of providing mass storage for the system 600. In some implementations, the storage device 630 is a non-transitory computer-readable medium. The storage device 630 can include, for example, a hard disk device, an optical disk device, a solid-date drive, a flash drive, magnetic tape, or some other large capacity storage device. The storage device 630 may alternatively be a cloud storage device, e.g., a logical storage device including multiple physical storage devices distributed on a network and accessed using a network.

The input/output device 6940 provides input/output operations for the system 600. In some implementations, the input/output device 640 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device includes driver devices configured to receive input data and send output data to other input/output devices, e.g., keyboard, printer and display devices (such as the touch screen display 218 of FIG. 2). In some implementations, mobile computing devices, mobile communication devices, and other devices are used.

In some implementations, the system 600 is a microcontroller. A microcontroller is a device that contains multiple elements of a computer system in a single electronics package. For example, the single electronics package could contain the processor 610, the memory 620, the storage device 630, and input/output devices 640.

Although an example processing system has been described in FIG. 6, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of nonvolatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments have been described. Nevertheless, it will be understood that various modifications may be made without departing from the spirit and scope of what has been described herein. Accordingly, other embodiments are within the scope of the following claims.

What is claimed is:

1. A medical system, comprising:
    a medical treatment machine configured to perform a medical treatment on a patient;
    a rules based engine configured to
        estimate a local inventory of a medical item, at least partly, based on a quantity of the medical item in a prior order and a date of the prior order, wherein the local inventory is used to supply the medical treatment machine with the medical item,
        determine that there is a current or anticipated shortage in quantity of the medical item by comparing (i) the estimated local inventory of the medical item to (ii) information related to a consumption rate of the medical item at the local inventory, and
        generate, based on the current or anticipated shortage of the medical item, a recommended order for the medical item to be placed, the recommended order including a recommended quantity for the medical item; and
    a control unit configured to
        receive the recommended order from the rules based engine,
        provide, to a user of the medical treatment machine, an output indicating the recommended order,
        receive, from the user, a user input confirming, rejecting, or modifying the recommended order, and
        transmit, to an order management system that is remote from the control unit, an instruction for an order for the medical item based on the user input regarding the recommended order, and
    wherein the order management system is configured to place the order for the medical item based on the instruction.

2. The medical system of claim 1, wherein the control unit is part of the medical treatment machine.

3. The medical system of claim 1, further comprising a gateway device that includes the control unit, wherein the gateway device is configured to communicate with the medical treatment machine through a wireless connection.

4. The medical system of claim 3, wherein the gateway device is configured to communicate with one or more remote systems through a cloud-based application.

5. The medical system of claim 4, wherein the one or more remote systems comprises at least one of the medical treatment machine, the order management system, and the rules based engine.

6. The medical system of claim 3, wherein the gateway device is configured to provide two-way conversational capability between the user and the gateway device by receiving audio from the user and generating a response signal to the user.

7. The medical system of claim 6, further comprising a speaker, wherein the control unit is further configured to
    cause the speaker to generate a spoken response based on the response signal;
    receive an audio input from the user;
    identify one or more spoken words based on the audio input; and
    cause the medical treatment machine to perform a treatment action based on the identified one or more spoken words.

8. The medical system of claim 1, wherein the recommended order differs from the prior order in at least the recommended quantity of the medical item.

9. The medical system of claim 1, wherein the rules based engine is further configured to estimate the local inventory of the medical item at a specific frequency.

10. The medical system of claim 1, further comprising a microphone configured to receive audio input from the user, wherein the control unit is further configured to
    identify a user parameter in the audio input received at the microphone, and
    cause the medical treatment machine to set or modify a treatment parameter based on the identified user parameter.

11. The medical system of claim 1, wherein the current or anticipated shortage of the medical item is further determined based on one or more of an expected rate of consumption of the medical item, a shipping time of the medical item, a frequency of use of the medical item, an availability of the medical item, an expected delay in shipping of the medical item, or a duration required to ship the medical item.

12. The medical system of claim 1, wherein the rules based engine is located at the medical treatment machine or at the order management system.

13. The medical of claim 1, wherein the user input includes spoken words.

14. The medical system of claim 1, wherein the user input includes an audio, and wherein the control unit is further configured to
    identify spoken words in the audio; and
    generate the instruction based on the identified spoken words.

15. The medical system of claim 1, wherein the medical treatment machine comprises a dialysis machine.

16. A method executed by a medical system configured to perform a medical treatment on a patient, the method comprising:
- estimating a local inventory of a medical item for the medical treatment, at least partly, based on a quantity of the medical item in a prior order and a date of the prior order, wherein the local inventory is used to supply the medical system with the medical item;
- determining that there is a current or anticipated shortage in quantity of the medical item by comparing the estimated local inventory of the medical item to information related to a consumption rate of the medical item at the local inventory;
- generating, based on the current or anticipated shortage of the medical item, a recommended order for the medical item to be placed, the recommended order including a recommended quantity for the medical item;
- providing, to a user, an output indicating the recommended order;
- receiving, from the user, a user input confirming, rejecting, or modifying the recommended order; and
- transmitting to a remote order management system, an instruction for an order of the medical item based on the user input, wherein the order management system is configured to place the order for the medical item based on the instruction.

17. The method of claim 16, further comprising identifying spoken words in the user input, wherein the user input is in form of audio, and wherein the order is placed based on the identified spoken words.

18. The method of claim 16, wherein the local inventory of the medical item is estimated at a predetermined frequency.

19. The method of claim 16, further comprising:
- receiving audio input from the user;
- identifying a user parameter in the audio input; and
- causing a medical treatment machine to set or modify a treatment parameter, or to perform a treatment action based on the identified user parameter.

20. One or more non-transitory computer-readable media storing instructions operable to cause a medical treatment system to perform operations comprising:
- estimating a local inventory of a medical item, at least partly, based on a quantity of the medical item in a prior order and a date of the prior order, wherein the local inventory is used to supply the medical treatment system with the medical item,
- determining that there is a current or anticipated shortage in quantity of the medical item by comparing the estimated local inventory of the medical item to information related to a consumption rate of the medical item at the local inventory;
- generating, based on the current or anticipated shortage of the medical item, a recommended order for the medical item to be placed, the recommended order including a recommended quantity for the medical item;
- providing, to a user, an output indicating the recommended order;
- receiving, from the user, a user input confirming, rejecting, or modifying the recommended order; and
- transmitting to a remote order management system, an instruction for an order of the medical item based on the user input, wherein the order management system is configured to place the order for the medical item based on the instruction.

* * * * *